United States Patent [19]

Bowes et al.

[11] Patent Number: 4,861,894
[45] Date of Patent: Aug. 29, 1989

[54] PYRIDINE AND ALKYLPYRIDINE SYNTHESIS USING A CRYSTALLINE SILICATE CATALYST HAVING THE ZSM-5 STRUCTURE

[75] Inventors: Emmerson Bowes, Hopewell, N.J.; Tsoung Y. Yan, Philadelphia, Pa.

[73] Assignee: Mobil Oil Corp., New York, N.Y.

[21] Appl. No.: 60,544

[22] Filed: Jun. 11, 1987

[51] Int. Cl.$^4$ .................. C07D 213/10; C07D 213/12
[52] U.S. Cl. ...................................... 546/251; 546/250
[58] Field of Search ............................... 546/250, 251

[56] References Cited

U.S. PATENT DOCUMENTS

| | | | |
|---|---|---|---|
| 2,807,618 | 9/1957 | Cislak et al. | 546/253 |
| 3,728,408 | 4/1973 | Tobias | 568/822 |
| 3,946,020 | 3/1976 | Minato et al. | 502/263 |
| 4,147,874 | 4/1979 | Beschke et al. | 546/251 |
| 4,149,002 | 4/1979 | Beschke et al. | 546/251 |
| 4,220,783 | 9/1980 | Chang et al. | 546/251 |
| 4,582,815 | 4/1986 | Bowes | 502/64 |

OTHER PUBLICATIONS

Advances in Catalysis, vol. 18, p. 344 (1968), Academic Press, Inc., New York, NY.

*Primary Examiner*—Alan L. Rotman
*Attorney, Agent, or Firm*—Alexander J. McKillop; Charles J. Speciale; Dennis P. Santini

[57] ABSTRACT

The present invention relates to an improved process for synthesizing pyridine or alkylpyridines comprising reacting ammonia with a carbonyl reactant in the presence of a catalyst composition which comprises a crystalline silicate having a silica/alumina mole ratio of at least 12 and a Constraint Index within the range of 1 to 12, the improvement comprising reacting said ammonia with said carbonyl compound in the presence of a catalyst composition which comprises (i) a crystalline silicate having a silica/alumina mole ratio of at least about 12, a Constraint Index of from about 1 to about 12, and an Alpha Value of less than about 50, and (ii) a binder of amorphous silica.

13 Claims, No Drawings

PYRIDINE AND ALKYLPYRIDINE SYNTHESIS USING A CRYSTALLINE SILICATE CATALYST HAVING THE ZSM-5 STRUCTURE

BACKGROUND OF THE INVENTION

1. Field of the Invention

This invention relates to an improved pyridine and alkylpyridine synthesis process. In the process for synthesizing pyridine or alkylpyridines by reacting ammonia and a carbonyl reactant in the presence of a catalyst comprising a crystalline silicate having a silca to alumina ratio of at least about 12 and a Constraint Index within the approximate range of 1 to 12, the present improvement comprises effecting higher activity, better selectively and better catalyst aging rate by using catalyst comprising said cystalline silicate having an Alpha Value of less than about 50 and a binder of amorphous silica.

2. Description of Prior Art

A method for synthesizing pyridine and alkylpyridines by reacting a carbonyl compound and ammonia over catalyst comprising a crystalline aluminosilicate zeolite having a silica/alumina mole ratio of at least 12/1 and a Constraint Index of from 1 to 12, which may or may not be composited with essentially any known binder material, including natural or synthetic materials, e.g. clays, alumina, silica-alumina and silica, and which may or may not contain a metal promoter, e.g. cadmium and copper, is taught in U.S. Pat. No. 4,220,783. U.S. Pat. No. 3,728,408 suggests the use of a catalyst comprising zeolite having a silica/alumina mole ratio greater than 10/1, preferably up to 200/1, more preferably with a maximum of 75/1, for conversion of organic polar compounds. Zeolites taught include Y, Beta, ZSM-5 with a silica/alumina ratio of up to 100, and mordenite. A reaction sugested by the latter patent is synthesis of methylpyridine from acetaldehyde and ammonia.

It is the improvement over the above cited references, each incorporated entirely herein by reference, which is the subject of the present invention.

The reaction of acetaldehyde or certain other low molecular weight aldehydes and ammonia either in the absence or presence of methanol and/or formaldehyde to yield pyridine and alkyl derivatives thereof has heretofore been carried out in the presence of amorphous silica-alumina composites containing various promoters. See, for example, U.S. Pat. No. 2,807,618. The yields of desired products using the latter catalysts have been poor.

Alkylpyridines have also been synthesized, as reported in Advances in Catalysis, Volume 18, page 344 (1968) Academic Press, Inc., New York, N.Y., by passing gaseous acetaldehyde and ammonia over the crystalline aluminosilicates NaX and H-mordenite. While initial conversion utilizing these materials as catalysts was high, catalyst deactivation by coking was rapid, providing a commercially unattractive system, characterized by poor catalyst stability.

U.S. Pat. Nos. 4,149,002; 4,147,874 and 3,946,020 teach synthesis of pyridine and/or alkylpyridines with different catalysts. The methods of U.S. Pat. Nos. 4,149,002 and 4,147,874 utilize a catalyst of highly dispersed aluminum silicate containing 3 to 30 weight percent aluminum oxide. The method of U.S. Pat. No. 3,946,020 uses a catalyst prepared by immersing silica-alumina or a silica-alumina mixture containing a promoter in an aqueous solution of ammonium halide.

A method for making an extruded silica-rich solid which may be useful as a catalyst for the present improved process is taught in U.S. Pat. No. 4,582,815 issued to E. Bowes.

SUMMARY OF THE INVENTION

This invention relates to an improved process for synthesizing pyridine and alkylpyridines by reaction of ammonia and a carbonyl compound selected from the group consisting of aldehydes containing from 2 to 4 carbon atoms and ketones containing from 3 to 5 carbon atoms in the presence of a catalyst comprising a crystalline silicate, characterized by a silica to alumina ratio of at least about 12 and a Constraint Index, hereinafter defined, in the approximate range of 1 to 12. The improvement of the present invention comprises higher activity, better selectivity and better catalyst aging rate by use of catalyst comprising said crystalline silicate having an Alpha Value of less than about 50 and a binder of amorphous silica.

EMBODIMENTS

In accordance with the present invention, there is provided a method for synthesizing pyridine and alkylpyridines by reacting ammonia and a carbonyl reactant constituting an aldehyde of 2 to 4 carbon atoms, a ketone of 3 to 5 carbon atoms or a combination thereof in the presence of a catalyst comprising a particularly defined crystalline silicate which has been found to afford a distinct improvement in activity, selectivity and stability for the production of pyridine and alkyl derivatives thereof over the aforenoted prior art processes.

The catalyst for use in the present process comprises a crystalline silicate exhibiting an Alpha Value of less than about 50 and a binder of amorphous silica. The binder portion of the catalyst will be from about 1 wt. % to about 60 wt. % of the catalyst composition, preferably from about 5 wt. % to about 40 wt. %.

When a binder other than silica, e.g. alumina or silica-alumina, is used for the present conversion reaction, all the benefits of this invention will not be realized, as demonstrated hereinafter.

When a catalyst composition is employed for the present conversion reaction which comprises a crystalline silicate having an Alpha Value of more than 50, all the benefits of this invention will not be realized, as demonstrated hereinafter.

The crystalline silicates for use herein include those having a Constraint Index of from about 1 to about 12. Members of this class of silicates have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size, e.g. greater than 8 Angstroms. The method by which Constraint Index is determined is described fully in U.S. Pat. No. 4,016,218, incorporated herein by reference for details of the method.

Constraint Index (CI) values for some typical materials are:

|  | CI (at test temperature) |
| --- | --- |
| ZSM-4 | 0.5 (316° C.) |
| ZSM-5 | 6-8.3 (371° C.-316° C.) |
| ZSM-11 | 5-8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest within the approximate range of 1 to 12.

The crystalline silicate for use herein includes those having the structure of ZSM-5, ZSM-11, ZSM-5/ZSM-11 intermediate, ZSM-12, ZSM-22, ZSM-23, ZSM-35, ZSM-38, ZSM-48, ZSM-50 and like materials ZSM-5 is described in greater detail in U.S. Pat. Nos. 3,702,886 and Re. 29,949, the entire contents of each being incorporated herein by reference. ZSM-11 is described in U.S. Pat. No. 3,709,979, the entire contents thereof being incorporated herein by reference. ZSM-5/ZSM-11 intermediate is described in U.S. Pat. No. 4,229,424, the entire contents thereof being incorporated herein by reference. ZSM-12 is described in U.S. Pat. No. 3,832,449, the entire contents thereof being incorporated herein by reference. ZSM-23 is described in U.S. Pat. No. 4,076,842, the entire contents thereof being incorporated herein by reference. ZSM-22 is described in U.S. Pat. No. 4,556,477, the entire contents thereof being incorporated herein by reference. ZSM-35 is described in U.S. Pat. No. 4,016,245, the entire contents thereof being incorporated herein by reference. ZSM-38 is described in U.S. Pat. No. 4,046,859, the entire contents thereof being incorporated herein by reference. ZSM-48 is described in U.S. Pat. No. 4,397,827, the entire contents thereof being incorporated herein by reference. ZSM-50 is described in U.S. Pat. No. 4,640,829, the entire contents thereof being incorporated herein by reference as to that description.

The Alpha Value of a catalyst material is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysts*, Vol. IV, pp. 522-529 (August 1965), each incorporated herein by reference as to that description. The catalyst tested in this Alpha Test must be in the hydrogen or hydronium form. This may be accomplished by hydrolysis of the material followed by calcination, by contact of the material with an ammonium salt or acid solution followed by calcination, or by calcination of the material if it contains a hydrogen precursor by way of its synthesis.

For the benefits of the present improved process to be fully realized, the catalyst must comprise a crystalline silicate having a Constraint Index of between about 1 and 12, and an Alpha Value of less than about 50, such as from about 1 to less than about 50, preferably from about 3 to about 30. Zeolite ZSM-5, for example, having a Constraint Index of 6 to 8.3 (371° C. to 316° C.) may have an Alpha Value much higher than 50. For instance, HZSM-5 with a silica/alumina mole ratio of 40 may exhibit an Alpha Value of about 250; and an Alpha Value of about 150 at a silica/alumina mole ratio of 70.

Therefore, for ZSM-5 to be a suitable crystalline silicate component of the catalyst for use herein, it must be synthesized or processed to have an Alpha Value of less than 50. This may be accomplished by any suitable means, such as by synthesizing the ZSM-5 with a higher silica/alumina mole ratio of from about 225 (Alpha Value=about 45) to about 2000 (Alpha Value=about 5). It may be accomplished by thermally treating or hydrothermally treating, e.g. steaming, a ZSM-5 having a higher Alpha Value to a point of having an Alpha Value of less than 50. An example of the latter means would be to contact a ZSM-5 having an Alpha Value of about 150 (such as one having a silice/alumina mole ratio of 70) with 100% steam at 550° C. for 2 hours, resulting in an Alpha Value of about 50 for said ZSM-5.

The specific crystalline silicate for use herein may be composited with the silica binder in any fashion resulting in a catalyst composition having from about 1 wt. % to about 60 wt. % of added binder silica. Such composition methods include, without limitation, blending freshly precipitated silica gel with the zeolite and spray drying for fluid bed application or initially drying and forming into particles by extrusion, pelletmill or granulation, or extrusion with silica gel preparations including colloidal silica. The silica source may be a xerogel like HiSil or Ultrasil or similar material and may be used alone or mixed with a dispersed silica, e.g. Ludox, or silicate from which silica is precipitated before or after compositing. The catalyst composition can also be made as an extrudate by the method of U.S. Pat. No. 4,582,815, issued to E. Bowes, the entire contents thereof being incorporated hereinby reference.

The present process for synthesis of pyridine and alkylpyridines is an improvement over the art. For instance, and as shown in examples which follow, the present process provides improved results when compared to the processes of U.S. Pat. Nos. 4,220,783 and 3,728,408.

Catalysts for use in this invention may include various catalytic metals, such as, for example, copper, zinc or a metal of groups VA (e.g. Bi), VIB (e.g. Cr, Mo and W) or VIII (e.g. Fe, Co, Ni, Ru, Rh, Pd, Ir and Pt) of the Period Table of Elements and combinations thereof. Preferred metals include copper, zinc, iron, platinum and palladium, alone or in combination with each other or another metal of the above-listed Periodic Table groups. The catalyst may comprise from about 0.1 wt. % to about 10 wt. %, preferably from about 0.5 wt. % to about 5 wt. %, incorporated catalytic metal or metals.

The above metal component can be impregnated into the compostion or intimately physically admixed therewith. Such component can be impregnated in or on it such as, for example, by, in the case of platinum, treating the composition with a solution containing a platinum metal-containing ion. Thus, suitable platinum compounds include chloroplatinic acid, platinous chloride and various compounds containing the platinum amine complex.

The catalyst for use in this invention may be dehydrated, at least partially. This can be done by heating to a temperature in the range of 200° C. to 595° C. in an inert atmosphere, such as air, nitrogen, etc., and at atmospheric, subatmospheric or superatmospheric pressures for between 30 minutes and 48 hours. Dehydration can also be performed at room temperature merely by placing the material in a vacuum, but a longer time is required to obtain a sufficient amount of dehydration.

The catalyst may be beneficially thermally treated prior to use in the present process by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. Hydrothermal treatment of the catalyst at from about 370° C. to about 550° C. may be beneficial.

The catalyst for use herein can be shaped into a wide variety of particle sizes for use in different types of reactors, namely fixed, moving and fluid beds. Generally speaking, the particles can be in the form of a powder, a granule, beads, fluidizable microspheres or a molded product, such as an extrudate having particle size sufficient to pass through a 2 mesh (Tyler) screen and be retained on a 400 mesh (Tyler) screen. In cases where the material is molded, such as by extrusion, it can be extruded before drying or partially dried and then extruded.

The carbonyl reactant for the present process may be an aldehyde containing 2 to 4 carbon atoms, a ketone containing 3 to 5 carbon atoms or mixtures of such aldehydes and/or ketones. Representative aldehydes include acetaldehyde, formaldehyde, propionaldehyde, acrolein, butyraldehyde and crotonaldehyde. Representative ketones include acetone, methyl ethyl ketone, diethyl ketone and methyl propyl ketone. The reactants for the present improved process may be in the presence of up to about 50 wt. % water.

The present process is carried out in a fixed bed, moving bed or fluid bed reactor at a pressure of from 0 psig to about 1000 psig, preferably from about 10 psig to about 500 psig; an average reactor temperature of from about 700° F. to about 1100° F., preferably from about 750° F. to about 1000° F.; and a weight hourly space velocity (WHSV based on carbonyl) of from about 0.1 hr$^{-1}$ to about 10 hr$^{-1}$, preferably from about 0.5 hr$^{-1}$ to about 5 hr$^{-1}$.

In order to more fully illustrate the nature of the invention and the manner of practicing same, the following examples are presented.

EXAMPLE 1

Crystalline ZSM-5 is prepared as in U.S. Pat. No. 3,702,886 with a silica/alumina mole ratio of 70/1. The ZSM-5 is made into the hydrogen form by NH$_4$Cl exchange followed by calcination. The HZSM-5 thus prepared has an Alpha Value of 150.

The HZSM-5 is then composited with alpha-alumina monohydrate and formed by extrusion to be composed of 65 wt. % HZSM-5 with an Alpha Value of 150 and 35 wt. % alumina binder.

EXAMPLE 2

Another sample of ZSM-5 is made in the same fashion as in Example 1, except with a silica/alumina mole ratio of 225/1. This ZSM-5 is made into the hydrogen form by the method of Example 1, and found to have an Alpha Value of about 45.

The HZSM-5 of this example is then composited with silica binder material and formed by extrusion to be composed of 65 wt. % HZSM-5 with an Alpha Value of about 45 and 35 wt. % silica binder.

EXAMPLE 3

Each catalyst of Examples 1 and 2 are teseted at the following conditions:

Feed Composition acetaldehyde/formaldehyde mole/mole=1.4/1
ammonia/carbonyl compound, mole/mole=1.5/1
water, wt. %=50

Reaction Conditions pressure=15 psig
temperature=788° F. inlet, 945° F. outlet
weight hourly space velocity (based on acetaldehyde)=1.5 $hr^{-1}$ Due to the exothermic reaction, the reactor temperature increases along the bed, reaching a peak of and leveling off at 945° F. As the catalyst ages during reaction, the temperature peak moves down through the catalyst bed. The rate of the temperature peak movement, in cm/hour, is a measure of catalyst stability, i.e. the slower this rate, the more stable the catalyst.

The reaction and product from the reactor are analyzed with the following results:

| Catalyst of | Example 1 | Example 2 |
|---|---|---|
| Conversion of acetaldehyde, wt. % | 57 | 61 |
| Yield, wt. % | | |
| pyridine | 43 | 47 |
| picolines | 14 | 14 |
| Pyridine Selectivity, % | 75 | 77 |
| Catalyst Aging Rate, cm/hr | 2 | 1 |

It is clear from the above results that the present process is an improvement over the prior art represented by use of the Example 1 catalyst. The catalyst for use herein is more stable by 50%, more active by 4% and more selective by 2% as shown above.

We claim:

1. In a process for synthesizing pyridine or alkylpyridines comprising reacting ammonia with a carbonyl reactant at reaction conditions suitable to synthesize said pyridine or alkylpyridines in the presence of a catalyst composition which comprises a crystalline silicate, the improvement comprising reacting said ammonia with said carbonyl at reaction conditions suitable to synthesize said pyridine or alkylpyridines in the presence of a catalyst composition which comprises (i) a crystalline silicate having the structure of ZSM-5 and an Alpha Value of less than about 50, and (ii) a binder of amorphous silica.

2. The process of claim 1 wherein said carbonyl reactant is selected from the group consisting of an aldehyde of 2 to 4 carbon atoms, a ketone of 3 to 5 carbon atoms and a combination thereof.

3. The process of claim 1 wherein the amorphous silica portion of said catalyst composition is from about 1 wt. % to about 60 wt. % of said catalyst composition.

4. The process of claim 3 wherein said binder portion is from about 5 wt. % to about 40 wt. %.

5. The process of claim 1 wherein said Alpha Value is from about 3 to about 30.

6. The process of claim 1 wherein said catalyst composition has been thermally treated at a temperature of from at least about 370° C. to about 925° C.

7. The process of claim 1 wherein said catalyst composition has been hydrothermally treated at a temperature of from about 370° C. to about 550° C.

8. The process of claim 1 wherein said carbonyl reactant is selected from the group consisting of acetaldehyde, formaldehyde, propionaldehyde, acrolein, butyraldehyde, crotonaldehyde, acetone, methyl ethyl ketone, diethyl ketone, methyl propyl ketone and mixtures thereof.

9. The process of claim 1 wherein said reacting is in the presence of water.

10. The process of claim 1 wherein said reaction conditions include a reactor pressure of from 0 psig to about 1000 psig, an average reactor temperature of from about 700° F. to about 1100° F., and a weight hourly space velocity, based on carbonyl, of from about 0.1 $hr^{-1}$ to about 10 $hr^{-1}$.

11. The process of claim 1 wherein said catalyst composition is in the form of extrudate, beads or fluidizable microspheres.

12. The process of claim 1 wherein said reacting of ammonia with a carbonyl reactant is in a fluidized bed reactor and said catalyst composition is in the form of fluidizable microspheres.

13. The process of claim 1 wherein said reacting of ammonia with a carbonyl reactant is in a fixed bed reactor and said catalyst composition is in the form of extrudate.

* * * * *